US006514703B1

(12) United States Patent
Dupret et al.

(10) Patent No.: US 6,514,703 B1
(45) Date of Patent: Feb. 4, 2003

(54) METHOD FOR SEPARATING AND CHARACTERIZING FUNCTIONS POTENTIALLY PRESENT IN A BIOLOGICAL SAMPLE CONTAINING NUCLEIC ACIDS

(75) Inventors: Daniel Dupret, Calvisson (FR); Jean-Michel Masson, Toulouse (FR); Fabrice Lefevre, Nîmes (FR)

(73) Assignee: Proteus S.A., Nimes (FR)

( * ) Notice: Subject to any disclaimer, the term of this patent is extended or adjusted under 35 U.S.C. 154(b) by 0 days.

(21) Appl. No.: 09/722,392

(22) Filed: Nov. 28, 2000

(30) Foreign Application Priority Data

Feb. 12, 1998 (FR) .............................. 98/10337

(51) Int. Cl.$^7$ ........................ C12Q 1/68; C12P 21/06; A01N 63/00; A01N 43/04; C07K 1/00
(52) U.S. Cl. ........................ 435/6; 435/68.1; 435/69.1; 435/91.2; 424/93.21; 514/44; 530/350; 536/23.1
(58) Field of Search ........................ 435/6, 68.1, 69.1, 435/91.2; 424/93.21; 514/44; 530/350; 536/23.1

(56) References Cited

U.S. PATENT DOCUMENTS 5,571,690 A * 11/1996 Hecht
5,643,722 A * 7/1997 Rothschild et al.
6,037,329 A * 3/2000 Baird et al. ..................... 514/44
6,303,337 B1 * 10/2001 Rothschild et al. ........ 435/69.1

FOREIGN PATENT DOCUMENTS

| WO | Wo 86/05803 | 10/1986 |
| WO | WO 94/24303 | 10/1994 |
| WO | WO 96/32504 A2 * | 10/1996 |
| WO | WO 98/49275 | 11/1998 |
| WO | WO 99/32619 | 7/1999 |
| WO | WO 99/57130 * | 11/1999 ..................... 435/6 |

OTHER PUBLICATIONS

Bowers et al., "Isolation Sequencing and Expression of the Gene Encoding a Major Protein from the Backteriophage Associated with *Bartonella Henselae*", *Gene*, vol. 206, pp. 49–52; (1998).
Craig et al., "Plasmid cDNA–Directed Protein Synthesis in a Coupled Eukaryotic In Vitro Transcription–Translation System", *Nucleic Acids Research*, vol. 20, No. 19; pp. 4987–4995; (1992).
Fincham, J.R.S., "Genes as DNA Sequences", *Genetics*, pp. 385–398; (1983).

Mackow, E.R., et al., "DNA Amplification–Restricted Transcription–Translation: Rapid Analysis of Rhesus Rotavirus Neutralization Sites", *Proc. Natl. Acad. Sci. USA*; vol. 87; pp. 518–522; (1990).
Niehaus et al., "Cloning and Characterisation of a Thermostable α–DNA Polymerase From the Hyperthermophilic Archaeon *Thermococus* sp. TY", *Gene*, vol. 204, pp. 153–158; (1997).
Ohuchi et al., "In Vitro Method for the Generation of Protein Libraries Using PCR Amplification of a Single DNA Molecule and Coupled Transcription/Translation", *Nucleic Acids Research*, vol. 26, No. 19, pp. 4339–4346; (1998).
Pratt, J.M., "Coupled Transcription–Translation in Prokaryotic Cell–Free Systems", IRL Press, Oxford XP002102865, pp. 179–209 (Chapter 7); (1992).
Promega Corp.: "Promega: 1997 Catalog", Promega Corp., NSDOCID XP002102864, pp, 2, 117–136 (1997).
Southworth, M.W. et al., "Cloning of Thermostable DNA Polymerases from Hyperthermophilic Marine Archaea with Emphasis on *Thermococcus* sp.9°N–7 and Mutations Affecting 3'–5' Exonuclease Activity", *Proc. Natl. Acad. Sci. USA*, vol. 93, pp. 5281–5285; (1996).
Southworth, M.W et al., "Control of Protein Splicing by Intein Fragment Reassemby", *The EMBO Journal*, vol. 17, pp. 918–926;(1998).
Stratagene: "Stratagene: 1995 Catalog", Stratagene USA, NSDOCID XP002102863, pp. 284–285 (1995).
Negishi et al., "Identitfication and cDNA cloning of single–stranded DNA binding proteins that interact with the region upstream of the human c–myc gene," 1994, Oncogene, vol. 9, pp. 1133–1143.*
Kruger et al., "Characterization of the mcrBC region of *Escherichia coli* K–12 ild–type and mutant strains", *Gene*, (1992), vol. 114, pp. 1–12.*

* cited by examiner

*Primary Examiner*—Jeffrey Fredman
*Assistant Examiner*—Arun K. Chakrabarti
(74) *Attorney, Agent, or Firm*—Hunton & Williams (57) ABSTRACT

The present invention is directed to a process for the separation and characterization of the functions potentially present in a biological sample containing nucleic acids, characterized in that it comprises the steps of preparation of nucleic acid fragments starting from said sample, association of each one of said fragments with a vector molecule, isolation of each fragment associated with a vector molecule or with a part of each construction composed of a fragment associated with a vector molecule, in vitro treatment of each fragment associated with a vector molecule or of a part of each construction composed of a fragment associated with a vector molecule to obtain transcripts, and testing of the function of the transcripts or of the proteins encoded thereby after translation of said transcripts.

37 Claims, 7 Drawing Sheets

FIG. 1

→ HYBRIDIZATION ZONE FOR PCR AMPLIFICATION

METHOD FOR SEPARATING AND CHARACTERIZING FUNCTIONS POTENTIALLY PRESENT IN A BIOLOGICAL SAMPLE CONTAINING NUCLEIC ACIDS

The present invention has for its object a process permitting separation of the functions potentially present in a biological sample containing nucleic acids and the characterization of said function, by protein expression in vitro after transcription and translation of DNA fragments. The characterization of a function according to the process of the invention can be done among other things by the biochemical analysis of this function and optionally by the cloning or the sequencing of the polynucleotide sequence corresponding to each of the functions possibly present in the studied sample.

In this way, the process according to the present invention more particularly permits the identification and the isolation of genes or of the corresponding proteins possessing a determined or determinable function.

The search for new genes and/or proteins encoded thereby constitutes an important objective of numerous molecular biology laboratories. In effect, the genetic and cellular therapy or the creation of transgenic animals or plants has caused new hopes for human or animal health, diagnoses and feeding, but requires, among other things, the identification of numerous genes and/or protein activities. Thus, numerous techniques exist for the isolation and the screening of genes by cloning and expression.

One of these techniques called "genomics" comprises the sequencing of a part or the totality of the organism's genome, then searching for homology with already identified sequences in data libraries of potentially coding sequences. Once identified, these sequences are to be subcloned and expressed in order to verify that they effectively code for the sought-after property. In addition to the time necessary for its implementation, this technique presents the disadvantage of being capable of identifying only functions homologous to those that are already known and referenced in the databases.

Proteomics is a second possible approach for looking for interesting properties. It consists of extracting the proteins expressed by a microorganism and then purifying them. Each purification fraction is then tested by detecting which one contains the sought-after property. The primary disadvantage of this technique resides in the fact that it does not permit having a direct link between the detected property and the gene that permits the expression of this property. The second disadvantage of this approach is that it does not permit the detection of the properties that have not been induced in the starting microorganism.

A third technique for detecting a function expressed by a microorganism consists of using expression cloning. This method has as a principle the extraction of the DNA of the starting microorganism, fragmenting it and inserting it in an expression vector in vivo that is transformed in a host. This host is selected for its ability to express the genes of the starting microorganism. In the same fashion the vector is always selected for its compatibility with the expression host. The expression cloning technique is used in context of the search for a function in a microorganism having genetic characteristics close to one of the existing host (same codon usage, same GC percentage). In the case of the search for a function starting with a large number of microorganisms of genetically varied origin, the expression cloning method becomes non-usable, the hosts no longer being capable of expressing the heterologous genes that are provided to them.

Additionally, expression cloning like other prior art processes for isolating and screening of genes presents a number of disadvantages:

the cellular toxicity of the transcription and translation products, which can induce genetic recombinations in order to mitigate these toxicity problems, the poor representativity of the library used, the implementation time, the low compatibility between the sequence of the cloned gene and the punctuation of the expression of the vector used, highly variable expression levels, codon usage problems, refolding and post-translational problems, the problem posed by the influence of the physiological state of a cell on the expression level of the proteins when the protein activity is sought directly in the original cellular extracts, a high difficulty of automation.

The present invention precisely aims to offset these disadvantages by offering a fast and effective method for the identification of a function associated with a polynucleotide sequence contained in a biological sample containing nucleic acids, and permitting the isolation of said sequence.

This goal is achieved thanks to a process for the separation and the characterization of the functions potentially present in a biological sample containing nucleic acids, characterized in that it includes the following steps:

a) the preparation of nucleic acid fragments starting from said sample, b) the association of each of said fragments with a vector molecule, c) the isolation of each fragment associated with a vector molecule or with a part of each construction composed of a fragment associated with a vector molecule of step (b), d) the in vitro treatment of each fragment associated with a vector molecule or of a part of each construction composed of a fragment associated with a vector molecule from step (c) in order to obtain transcripts, e) the test of a function of the transcripts obtained at step (d) or of proteins for which they code after translation of said transcripts.

The process of the invention offers the advantage of enabling the carrying out of:

a test of the properties of the transcripts of step (d), when they have advantageous properties of the tRNA, rybozyme type, or a test of the properties of the proteins coded for by said transcripts.

In each case where the functions of the proteins encoded by the transcripts obtained at step (d) are tested, the process of the invention comprises at step (d) the treatment of said transcripts in vitro with a cellular extract permitting their translation to protein, then the test of a function of said proteins by any appropriate means.

By function in the sense of the present invention is understood more particularly the property that can be encoded by a polynucleotide sequence. This property can for example be an enzymatic activity or an affinity if said sequences codes for a protein, or an endonuclease activity for example if said sequences codes for a catalytic mRNA.

Thus, the process of the invention permits not only the detection of a function, but also the characterization of this function from a biochemical point of view. If the function is an enzymatic activity for example, it can relate to the analysis of the optimal conditions of functioning (pH, temperature, salts concentration), of the kinetic parameters (Vm, Km), of the inhibition parameters (Ki). If the function is an affinity, it can relate to the determination of the Kd, or of the molecule having the most affinity for this protein. It can also relate to the determination of the size of the translated protein or of the mRNA transcript, and optionally of the sequencing of the corresponding gene.

By biological sample is understood any sample liable to contain nucleic acids, such as a soil, plant, blood, human or animal, water, microbial, cellular or viral culture, biopsy, etc. sample, but these samples can equally correspond to amplification products (PCR, NASBA, etc . . . ), genomic DNA, synthetic DNA, mRNA, or any product of nucleic acids resulting from treatments currently used by a person skilled in the art.

By vector molecule is understood one or several polynucleotide sequences comprising at least a transcription promoter for step (d) and possibly a substance facilitating the isolation of the step (c) fragment. Optionally this substance can be one or several molecules of streptavidine or of biotin, of the polypyrol group, of antibodies, a single or double-stranded polynucleotide sequence, a DNA plasmid vector preferably not containing sequences permitting the in vivo expression of the associated fragment, or any other compound permitting the isolation of the fragment associated with step (c).

By isolation at step (c) of the process of the invention is understood the subdivision of the batch of fragments obtained at step (b) in subsets, a subset that can be composed of a single or of several nucleic acid fragments.

Step (a) for the preparation of the nucleic acid fragments of the process of the invention can comprise an extraction phase if the nucleic acids are not directly accessible in the biological sample, for example in the case of nucleic acids contained in cells, viruses, blood, organic elements, etc . . . This extraction phase is thus included in step (a) for preparation of nucleic acid fragments. Similarly in the case where the biological sample is composed of mRNA, a step of RT-PCR is necessary to prepare the nucleic acid fragments of step (a).

According to a particularly preferred embodiment of the invention, the vector molecule is composed of two polynucleotide sequences each comprising at least one transcription promoter. Each one of these sequences is associated with an end of one of the fragments obtained at step (a).

According to an advantageous embodiment of the process of the invention, the transcription promoter or promoters carried by the vector molecule is/are a promoter or promoters of the strong type, such as the RNA polymerase transcription promoter of the T7, SP6, Qβ or λ phage.

Thus, a particular application of the process of the invention permits identification of a polynucleotide sequence and/or the corresponding protein, possessing a function, starting from a sample containing nucleic acids. This goal is attained according to a process characterized in that it comprises the following steps:

a) the preparation of nucleic acid fragments starting from said sample, b) the insertion of each one of said fragments in a vector so as to create recombinant vectors, c) the isolation of each recombinant vector or of a part of this recombinant vector by any appropriate means, d) the in vitro treatment of the vector or of a part of the recombinant vector isolated at step (c) to obtain transcripts, e) the test of a function of the transcripts obtained at step (d) or of the proteins encoded thereby by any appropriate means after translation of said transcripts.

By recombinant vector in the application of the above process of the invention is understood a vector, for example, plasmidic, in which a fragment has been introduced, and by part of this vector, the part of the recombinant vector containing the fragment obtained at step (a) and the elements necessary for the implementation of the steps (d) and optionally (e).

The steps of the process of the invention can be carried out successively without interruption by the same operator, advantageously on an automated device integrating each of the steps, or can be carried out in a discontinuous fashion, optionally by different operators.

The transcription step (d) and the translation phase of step (e) of the fragments are also conjointly designated In Vitro Protein Expression reaction, also designated EPIV reaction. The EPIV reaction can be simultaneous, which means that the step (e) translation phase is carried out simultaneously with the step (d) transcription, or broken down into two distinct steps, transcription (d) and translation (e).

The uncoupling of the steps (d) and (e) permits optimization of the yields of each step, and thus production of greater quantities of proteins, which finds significant utility in the case of enzymes of weak specific activity.

This uncoupling also permits normalization of the formation of the step (e) products and enables later comparison of the different expressed functions.

The uncoupling out of the step (d) transcription and the step (e) translation equally permits avoiding the problems of degradation of the DNA template by nucleases if it was prepared by PCR. In effect, the components of the transcription reaction are less contaminated by the nucleases, in contrast to the translation extracts.

The uncoupling moreover permits the use of different translation extracts according to the origin of the DNA screened. In effect, the step (e) translation phase of the transcripts obtained during step (d) is advantageously carried out with a translation extract of the same origin or of a close origin to that of the biological sample on which the process of the invention is practiced. Thus, the correspondence between the origin of the transcript translation signals and the cellular extract is optimized for optimal translation effectiveness. By way of example, there can be cited the use of a translation extract of an extremophilic organism for the screening of a DNA library of the same organism or of another extremophilic organism (thermophiles, halophiles, acidophiles, etc . . . ) or also a translation extract of eukaryotic cells for the screening of a eukaryotic DNA library. These respective extracts are likely to improve the effectiveness of the process. These extracts are selected for their capacity to translate the transcripts at step (e).

The process of the invention is notable in that it implements a correspondence between the expression punctuation of the transcripts of step (d) and the translation extracts used. These extracts are also characterized in that either they do not contain the sought-after property, or they contain it but it is not detectable under the conditions of the test carried out for detecting the sought-after function. It concerns for example the use of a translation extract containing a mesophilic beta-galactosidase activity permitting translation of a thermophilic beta-galactosidase mRNA and the detection of the activity of the latter at high temperature, which eliminates the mesophilic beta-galactosidase activity.

Depending of the genetic origin of the fragments obtained at step (a), (i.e. DNA of Gram positive or negative, eukaryotic, viral, etc. microorganisms), and of the function tested, different translation extracts can be used.

A particular embodiment of the process of the invention consists of using at step (a) a translation extract that is in fact a mixture of several translation extracts. It relates for example to a translation extract of *E. coli* over-expressing a chaperon A protein mixed with a translation extract of *E. coli* over-expressing a chaperon B protein. Any type of mixture can be contemplated from the moment that it corresponds to the characteristics described above. In the same manner, it is possible to use a translation extract in which one or several specific tRNAs of one or several codons are added. The translation extracts obtained in this way thus permit translation of the mRNA containing specific codons, such as for example the translation of an mRNA containing an amber codon by adding in the translation extract one of tRNA suppressor(s).

The treatment of step (e) with a translation extract can also be carried out with a universal translation extract whatever be the origin of the sample such as for example an extract of *E. coli* and/or any other cellular extract or extracts supplemented or not by molecules of interest such as those, for example, indicated previously (tRNA, chaperon . . . ).

It is equally possible to add to the translation extract of step (e) one or several substances favoring a more effective refolding or maturation of the expressed proteins, such as for example chaperons, detergents, sulfobetaines, membrane extracts, etc . . .

The test of a function of the proteins synthesized at step (e) can be carried out by any appropriate means permitting for example the detection of the sought-after enzymatic activity or activities. This embodiment will more particularly be applied during the search for enzymes with original properties, such as for example thermostable enzymes active at high temperature, in an acidic medium, in a medium of high salt concentration, etc . . . , starting from a DNA sample resulting from an extremophilic organism or organisms. These extremophilic enzymes, often active under conditions close to the physiological conditions of the strains which produce them (temperatures, salinity, pH, etc . . . ) are particularly interesting tools for numerous industrial processes (agribusiness, animal nutrition, paper, detergents, textile industries etc . . . ), where they can be substituted for their mesophilic homologues.

The process of the invention offers the advantage of being capable of carrying out:
  a test of the properties of the step (d) transcripts, when they have advantageous properties of the tRNA, rybozyme type, or
  a test of the properties of the proteins encoded by said transcripts.

In the case of a ribozyme having an endonuclease activity for example, it is possible to detect this activity by using a nucleotide matrix having a fluorescent group at one end and a "quencher" group at the other. In case of cutting of the matrix by the ribozyme, the fluorescent group is separated from the "quencher" group, which frees the fluorescence from the first.

In the case of a tRNA, it is possible to use for example a fraction of the reaction potentially containing this tRNA and to put it in an in vitro translation reaction containing the mRNA of a reporter gene of which one of the codons can be read only by the sought-after tRNA. If the activity of the reporter is detected, this means the tRNA was present in the initial fraction and that it permitted the in vitro translation of the reporter mRNA.

In the context of demonstrating an enzymatic activity, any type of specific substrate can be contemplated by a person skilled in the art for demonstrating the presence or the absence of the sought-after function at step (e). All transformation(s) of the substrate(s) by the sought-after function(s) can be detected by any method known by a person skilled in the art (fluorimetry, colorimetry, absorbance, viscosity, etc . . . ).

In the case of the demonstration of an affinity, it is possible for example to use, according to the sought-after affinity: antibody-antigen, double stranded DNA binding protein, receptor-ligand, etc . . . , tests such as radio-labeled ligand fixation, an immunological detection comprising the immobilization of an antigen, its specific detection with the sought-after antibody, and the revelation of this sought-after antibody thanks to an anti-antibody antibody coupled to a reporter activity which can be revealed, or an antigen detection by using a goat antibody fixed on a support capable of recognizing the antigen, the antigen being able to be detected by a second rabbit antibody (sandwich formation) indirectly coupled or not to a reporter activity (alkaline phosphatase or peroxidase type).

One particular embodiment of the process consists at step (e) of testing, in parallel or in a simultaneous or non-simultaneous manner, different properties of the same or several functions.

Thus, the process of the invention is notable in that it not only permits the detection of the functions potentially contained in a biological sample, but also:
  their quantification, when these properties permit it such as for example enzymatic activities or affinities.
  their characterization, notably biochemical, such as for example the optimal conditions of functioning at temperature, pH, saline concentration, etc . . . , molecular weight, protein sequencing, and optionally sequencing of the corresponding polynucleotide sequence.

The process of the invention is also notable in that it is totally independent of the in vivo expression of the proteins. The cellular hosts, like microorganisms, if they are used, are used only for the isolation and amplification of the heterologous fragments. Consequently, the process of the invention permits avoiding all of the problems previously reported with expression cloning methods of the prior art. In particular, the process of the invention is of great interest in the identification of a gene expressing a cytotoxic protein. In this sense, the vector molecule associated with each fragment of step (b) can be a plasmidic vector preferably not permitting the expression of said fragment in vivo. By way of example of such a vector one can cite: pBR322 or pACYC184.

Advantageously, the fragments prepared at step (a) of the process of the invention are obtained by the action of one or several endonucleases on the nucleic acids of the biological sample or on the PCR products of said nucleic acids. These fragments can also be obtained by a mechanical action on theses nucleic acids, for example by passage in a syringe needle, disruption under pressure, sonication, etc.

In the particular embodiment of the process of the invention where the nucleic acids of the sample do not require fragmentation, such as for example genomic libraries, step (a) consists of preparing the fragments of this sample for step (b), for example by extraction, and/or purification and/or preparation of the ends for the association with vector molecules, for example the insertion in the plasmidic vector.

In a particular embodiment of the process of the invention, the fragments prepared at step (a) have a size of 1 to several dozen kb, preferably from 1 to 40 kb and advantageously from 1 to 10 kb when the sample comes from a prokaryote organism. Preferably, the fragments prepared at step (a) have a size on the order of 5 kb. In effect, the average size of a prokaryote gene is about 1000 base pairs. By using fragments of 5000 base pairs, it is possible to obtain clones carrying the complete gene with their proper ribosome-binding site. In the case where the DNA is of eukaryotic origin, the size of the fragments prepared at step (a) is much more important, advantageously on the order of several dozens to several hundreds of kilobases.

It can be noted that the fragments prepared at step (a) can carry a partial or entire operon.

The biological sample that the fragments of step (a) are prepared from can come from one or several identical or different prokaryotic organisms or eukaryotic cells or even viruses. It can for example be a sample of nucleic acids of a microorganism or of a mixture of microorganisms, or of eukaryotic tissue cells or of identical or different organisms. But the sample of nucleic acids can equally be composed of a sequence or of a library of a nucleic acid or of nucleic acids. The biological sample can be composed of known or unknown organisms and/or of known or unknown nucleic acids. The sample can also advantageously be composed of synthetic nucleic acids.

In the case of a eukaryotic DNA library, the transcription reaction can be completed by in vitro splicing and maturation reactions of the mRNA by using for example a nuclear extract (3).

The process of the invention assures a direct link between the function demonstrated at step (e) and the corresponding polynucleotide sequence. This process is therefore most particularly suited for detecting functions and identifying the corresponding genes starting from genomic DNA. By gene is understood a DNA fragment or sequence associated with a biological function.

As indicated previously, according to a particular embodiment of the process of the invention, the vector molecule associated with the nucleic acid fragments at step (b) is a plasmidic vector. In this case, at step (b) of the process of the invention, each fragment is inserted in a vector at the level of a cloning site or of a restriction cassette. This plasmidic vector is characterized in that it comprises an RNA polymerase promoter at one side of the cloning site and optionally an RNA polymerase terminator at the other side. It is also possible to design a vector comprising a cloning site surrounded by two different or identical RNA polymerase promoters and possibly flanked on both sides by a corresponding RNA polymerase terminator or terminators. These promoters and possibly terminators preferentially have the characteristic of not functioning in the microorganism that can be used for the separation of the recombinant vectors at step (c).

In the case where the vector does not possess an RNA polymerase promoter or promoters and/or optional terminator or terminators, or in the case where the RNA polymerase promoter or promoters and possible terminator or terminators are not adequate for carrying out step (d), this promoter or promoters and possible terminator or terminators can be inserted at step (c) of the process of the invention by any appropriate means. An advantageous embodiment of this insertion consists of carrying out a PCR with a set of primers carrying the sequences of the promoter(s) and terminator(s).

According to a particular embodiment of the process of the invention, the promoter(s) and possible terminator(s) are of the strong type such as for example those of the T7 RNA polymerase.

In the case where the vector molecule is a plasmidic vector, the isolation of the recombinant vector at step (c) can be carried out by transformation of host cells by the entirety of the recombinant vectors obtained at step (b) so as to create a library of clones, then by carrying out an extraction of the recombinant vector or of a part of the vector contained by each clone of the library by any appropriate means.

The extraction of the recombinant vector or of a part of the recombinant vector flanked by the RNA polymerase promoter(s) and possibly terminator(s) can be carried out by any method known by a person skilled in the art, such as by plasmid miniprep and possibly digestion or by PCR. An advantageous alternative consists of carrying out this PCR with oligonucleotides protected from 5' nucleasic attacks, notably from the nucleases contained in the translation medium, by phosphorothioate groups.

As previously indicated, the isolation at step (c) can be carried out by any physical, mechanical or chemical means such as for example a simple extreme dilution of the entirety of the fragments associated with the vector molecule at step (b). However, the isolation can also advantageously be carried out by using the properties of a specific substance included in the vector molecule, such as an antibody molecule, and the isolation of the fragment is carried by using the antibody-antigen affinity, or a biotin, and the isolation is carried out by using the biotin-streptavidine affinity, etc. . .

According to a particular embodiment of the process of the invention, a sorting of the fragments or the part of them each associated with a vector molecule obtained at step (c) is effected. For this, an EPIV reaction is carried out for each of the fragments or the part of them associated with a vector molecule obtained at step (c) by incorporating in the reaction mixture of the translation phase of step (e) a label of protein synthesis (biotinylated tRNA, modified amino acid, etc . . . ). Each EPIV reaction product is then analyzed, for example by ELISA, for the presence of an expressed protein. The fragments or the part of them associated with a vector molecule for which the EPIV reaction is negative are determined. These fragments do not possess an ORF on their insert. Following this pre-screening procedure, these fragments are eliminated from the following activity identification screenings linked to a protein. Such a pre-screening procedure permits a savings in time and in reactants in the case of a screening that is repetitive and not simultaneous from the same library.

According to a particular embodiment, the process of the invention is entirely carried out on a solid chip type support or a membrane or a nanotitration plate. The chip type support can be a glass plate, a nitrocellulose membrane or any other support known to a person skilled in the art. The fragments associated with the vector molecule are isolated on this chip type or nanotitration plate support, and the reactants permitting the implementation of the process of the invention are deposited on this support. The test of the sought-after function or functions can be directly conducted on the support after a possible washing of the latter. In the case where the vector molecule is a plasmidic vector and/or the process of the invention is carried out on a support, the colonies transformed by the recombinant vectors are transferred separately from the others on a same support, then lysed in situ (3) such that each colony can liberate on the support the copies of the recombinant vector that it contains. Another embodiment consists to separately loading on a same support each recombinant vector or part it. It is thus possible to deposit reactants permitting the carrying out of an EPIV reaction on the support having the deposited DNA according to one of the techniques described above. The test of a function can be directly conducted on the support after an optional washing of the latter.

The invention equally has for an object:
- a not yet known nucleic acid sequence identified and selected by the process of the invention,
- a fragment containing this nucleic acid sequence associated with a vector molecule,
- a plasmidic vector containing this sequence, a cellular host transformed by this nucleic acid sequence or by this vector, or
- a protein encoded by this sequence.

The invention equally relates to any library composed of:
- nucleic acid sequences isolated by the process of the invention,
- vector molecules associated with fragments containing these sequences,
- vectors containing said sequences,
- cellular hosts transformed by one (or some) of these sequences or by one of these vectors, or
- proteins encoded by said sequences.

The process of the invention offers the advantage as compared to the methods of the prior art of being capable of being automated. In the case where the vector molecule is a plasmidic vector, this automation can be conducted, for example, in the following manner:

Each recombinant vector of the library formed at step (b) can be put in culture on a support, in a microplate well by a Colony Picker type robot.

This culture can be used for a plasmidic extraction step carried out by a Biorobot 9600 (QIAGEN) type robot, or for a PCR amplification step implemented by a MultiProbe type machine (PACKARD) on a PTC 200 or PTC 225 (automated lid-MJ RESEARCH) type automatic thermocyler.

The optional purification of the PCR products can be conducted by the BioRobot 9600 automatic machine.

The EPIV reaction of steps (d) and (e) can be directed entirely by the MultiProbe robot. The tests of the functions of the transcripts obtained at step (d) can be effected on the robot pipetor and the reading of the results is obtained on a corresponding reader. If the transcription reaction is separated out from the translation reaction, the optional purification of the mRNA can be carried out by the BioRobot 9600.

The tests of the activity of the proteins synthesized at step (e) are carried out by the robot pipetor, and the reading of the results is obtained on the reader (spectrophotometry, colorimetry, fluorimetry, etc . . . , according to the test carried out) of micro plaques or by any other appropriate means.

Consequently, the invention also relates to an automated device for the implementation of the processes described previously comprising a layout of one or several supports, robots, automatic machines and readers optionally permitting the preparation of the sample at step (a) and optionally the carrying out of the step of association of the fragments with the vector molecule at step (b), optionally the isolation of said fragments associated with the vector molecule at step (c), and to carry out the implementation of the steps (d) and (e). By assuring an increased repetition flow of the process of the invention, or of a part of the process of the invention (steps (d) and (e)) this layout of automatic machines permits rapid searching of the functions starting from different nucleic acid samples.

Figure 1:
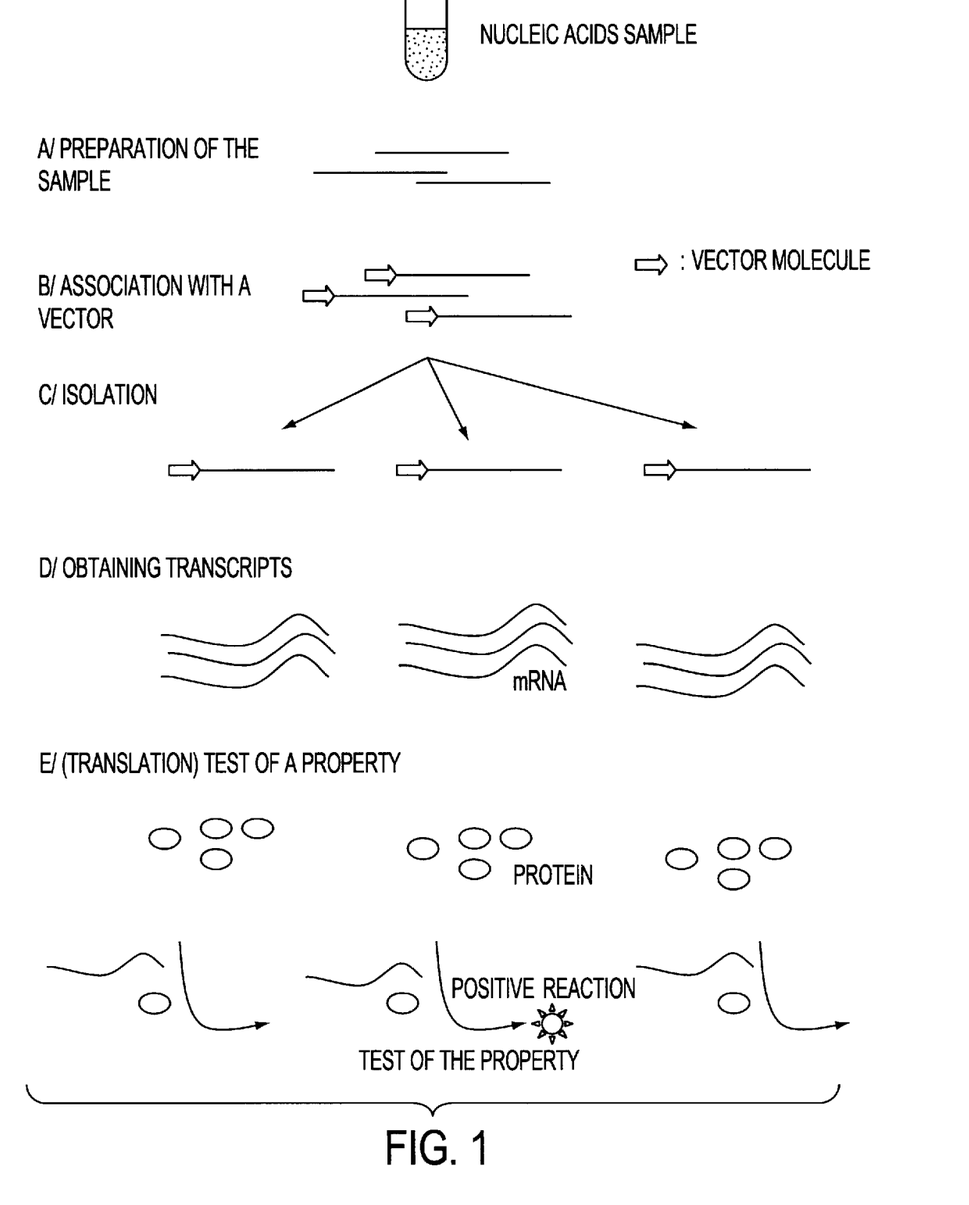
FIG. 1 is a schematic representation of an example of an embodiment of the process of the invention.
Figure 2:
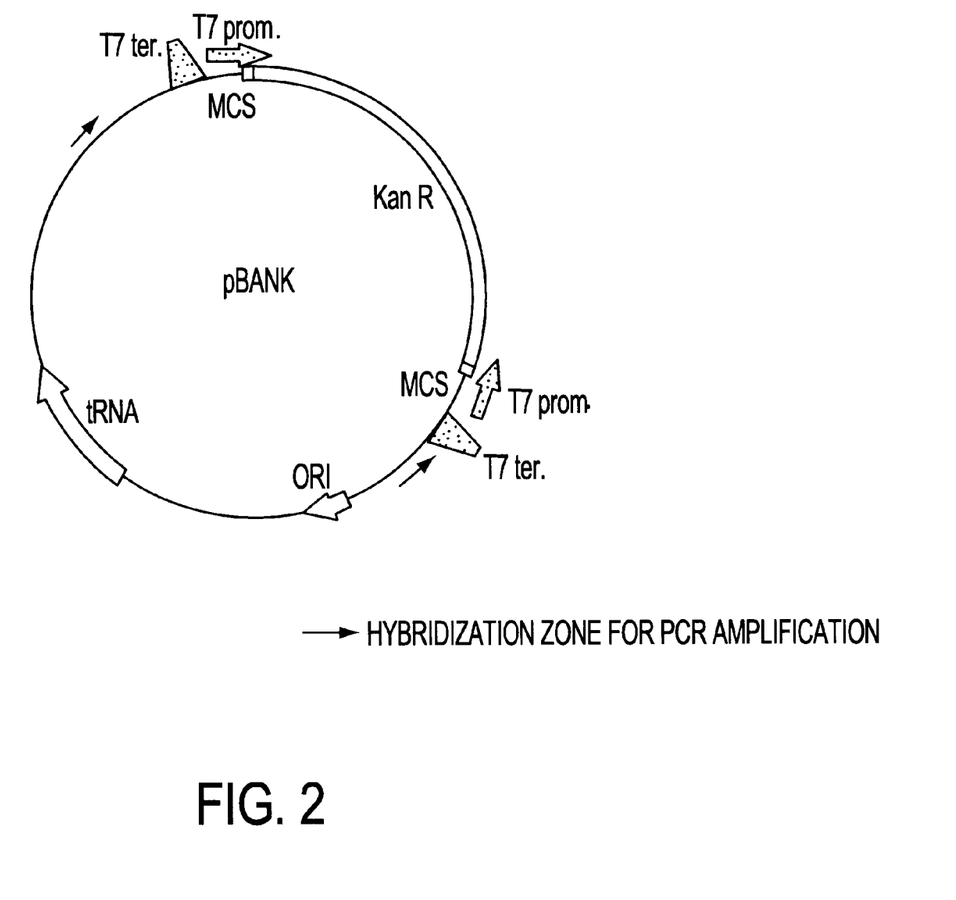
FIG. 2 represents an example of a cloning vector for the construction of a library according to the process of the invention.
Figure 3A:
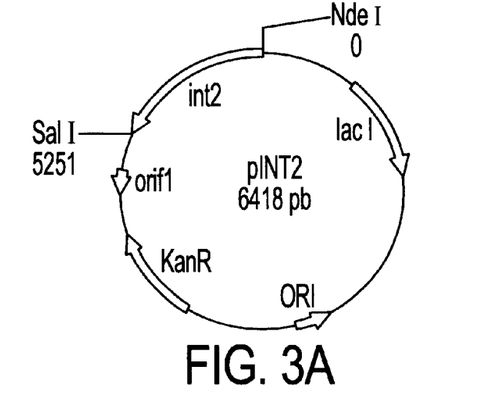
FIG. 3 represents an example of the plasmids pADH, PTEM, pET26-Tfu2, pLIPet pGFP used in the scope of the examples of carrying out the process of the invention.
Figure 3B:
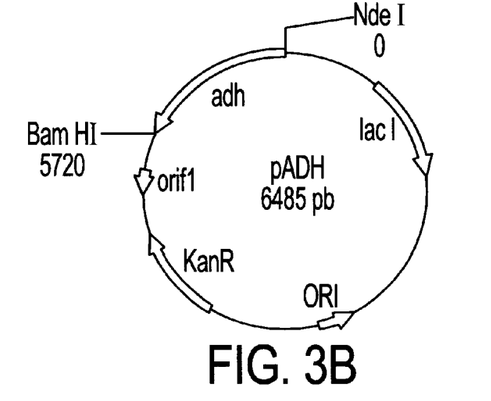
Figure 3C:
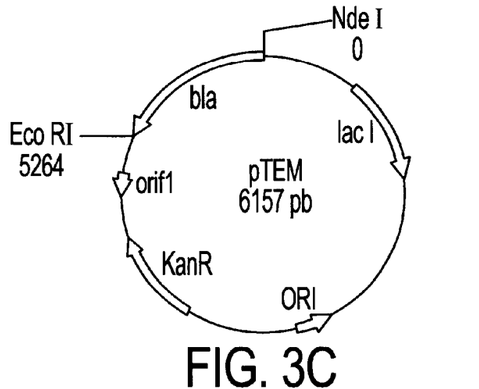
Figure 3D:
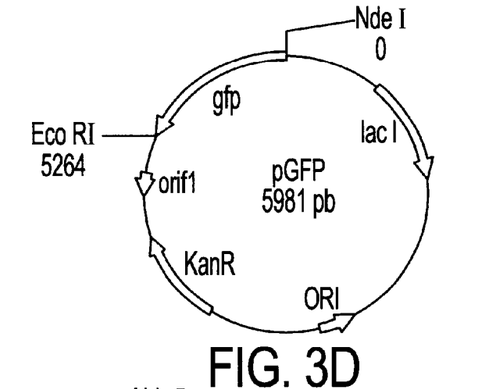
Figure 3E:
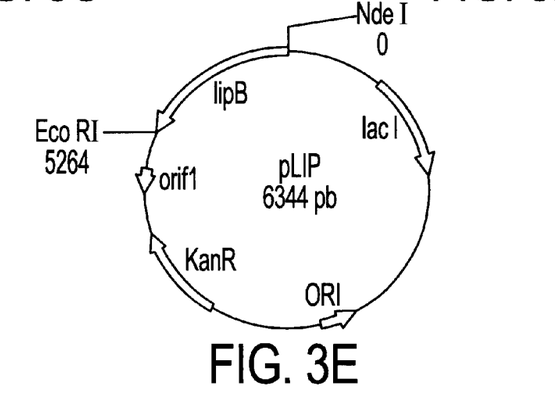

Any plasmidic vector having the characteristics defined previously can be used in the process of the invention. By way of example can be cited a vector represented at FIG. 2 and constructed in the following manner:

A plasmidic replication origin.

A cloning site surrounded by two identical promoters, such as that of the T7 RNA polymerase, or of any other strong RNA polymerase promoter, such as Qβ, T3, SP6, etc., and optionally flanked on both sides by the same RNA polymerase terminator. These promoters and terminator if it is present, preferably do not function in the microorganism used to separate the recombinant vectors. Such a construction permits transcription of a DNA fragment inserted in the cloning site, regardless of its sense of insertion. The probability of finding a good clone is therefore multiplied by two. The average size of a prokaryotic gene is about 1000 bp. By using prokaryotic DNA fragments of about 5000 bp to generate the library, it is highly probable that clones carrying the complete genes will be obtained, with their proper ribosome binding site (or RBS for Ribosome Binding Site). With this double promoter system, the gene is located in the worst case 2000 bases from the beginning of the mRNA, which permits effective expression of the corresponding protein by the process of the invention (as reported in the experimental hereinafter on the β-lactamase activity).

Optionally, some specific sequences on both sides of the terminators can be used as hybridization sites for a PCR amplification of the nucleic acid fragment carried by the vector.

A selection gene composed of a tRNA gene (4). Optionally, in parallel, an antibiotic resistance gene (or another type of selection gene) is inserted in the cloning site. This antibiotic selection is used only for the preparative amplification of the cloning vector. In effect, during the insertion of each one of said fragments of step (b), a DNA fragment is substituted for this resistance gene. This system has the advantage of not depending on an antibiotic selection, which raises problems of contamination and degradation of the antibiotic, and permits obtaining a recombinant vector not possessing an ORF other than that possibly introduced by the heterologous fragment. On the other hand, it permits a very rapid evaluation of the level of negative clones, by practicing a parallel spreading of a fraction of the library on minimum medium and on a medium containing the selection antibiotic.

The process of the invention is notable in that it permits looking in crude samples for nucleic acid functions and to characterize them and identify the corresponding nucleic acid sequence. In effect, it avoids the isolation of each microorganism present in this sample. The isolation of the microorganisms contained in a sample is known to give limited results, for only a few percent of the diversity of the microorganisms present are recovered. Moreover, the process of the invention offers a considerable time savings. The method of the invention permits the realization of a better result, since the screened biodiversity is of the order of 100%, in a time period of 5 to 10 days. Whereas the prior art methods permit isolation of around of 5% of the biodiversity of a sample over several weeks or even several months, as much time is necessary to screen these strains in order to detect a protein activity. The process of the invention is equally advantageous for searching for the protein activities in a given germ or cell. A genomic or cDNA library can be easily prepared and screened according to the process of the invention. In the case of a cDNA library, the vector molecule comprises a translation initiation sequence corresponding to the translation extract used at step (e). In addition to its rapidity, the process of the invention permits a freeing from the cellular physiology. It is thus possible to detect the protein activities without having to resolve problems of culture and of physiological states. The process of the invention permits directly going back up to the gene starting from the detection of a function of the organism. It also permits looking for a function in an organism potentially containing said function. This technique permits, thanks to its speed and its effectiveness, the screening of one or several functions of a large number of organisms from a collection and therefore to bring out its microbiological biodiversity. This process will find much of its utility in the identification of protein activities of industrial interest starting from isolated extremophilic organisms, or also from crude samples of said organisms.

Finally, the process of the invention finds an interest in the area of genomics. From its conception, it permits the identification of new genes without going through sequencing in the first step, because it permits going directly from the detection of a function to the sequence of the corresponding nucleic acid. Applied to the totality of the genomic DNA of an organism, the process of the invention permits attainment of the characterization of the total phenotype of this organism, which introduces the notion of "phenomics."

The invention also relates to a kit for the implementation of the process of the invention described previously. This kit comprises:

the means necessary for the preparation of the nucleic acid fragments at least one vector molecule at least one polymerization agent optionally at least one cellular translation extract the means necessary for the test of one or several functions the buffers necessary for the carrying out of the different steps This kit can be packaged in one or different containers.

Other advantages and characteristics of the invention will appear from the examples of carrying out the invention that follow and that refer to the annexed drawings in which.

MATERIALS

1) Strains and Plasmids

The vector pET26b+ is part of the family of pET vectors developed by Studier and Moffatt (8) and commercialized by the NOVAGEN Corporation. This vector permits expression of the genes under the control of the T7 phage promoter. The PinPoint™ (PROMEGA) vector carries the cat gene (coding for the chloramphenicol acetyltransferase) under the control of the T7 phage RNA polymerase. The vector pHS2-22-21 was constructed by introducing by reverse PCR the cutting site recognized by the intein 2 of the Tfu DNA polymerase positioned in the polycloning site of the plasmid pUC19. The vector pHS2-22-21 corresponds to pUC 19 containing the homing site (43 bp) of the intein or the site in which the intein gene is inserted.

The strain XL1-Blue [Tn10 proA$^+$B$^+$ lacI$^q$ Δ (lacZ)M15/ recA1 endA1 gyrA96 (Nal$^r$) thi hsdR17 ($r_k^-m_k^+$)supE44 relA1 lac) was used for the amplification of the plasmidic DNA.

2) Reagents

The restriction and modification enzymes reported in Table I below were used according to the recommendations of the suppliers.

TABLE I

| Enzyme | Concentration | Supplier |
| --- | --- | --- |
| Sca I | 10 U/µl | Appligene Oncor |
| Sal I | 8 U/µl | New England Biolabs |
| Nde I | 20 U/µl | New England Biolabs |
| Bam HI | 20 U/µl | New England Biolabs |
| Eco RI | 20 U/µl | New England Biolabs |
| T7 RNA polymerase | 50 U/µl | New England Biolabs |
| T4 DNA ligase | 400 U/µl | New England Biolabs |

The buffers used are described in Table II below.

TABLE II

| Buffers | Composition |
| --- | --- |
| T | Tris HCl 10 mM pH 8.0 |
| T7 RNA polymerase (10 X) | Tris HCl 400 mM pH 7.9, 60 mM MgCl$_2$, 20 MM spermidine, 10 mM DTT |
| IT2 (10X) | Tris-Oac 500 mM pH 8.0, 750 mM Mg(OAc)$_2$, 100 mM NH$_4$OAc |
| TADH (2X) | Glycine 100 mM (NaOH pH 10), 20 mM Butanol 1, 0.9 M NaCl, 4 mM NADP |
| LIP | KH$_2$PO$_4$ 0.1 M, pH 6.8, dioxane 5%, Thesit 5% |
| BETA | NaP 50 mM pH 7.0, 100 µg/ml Nitrocephine, 0.25 mM DMSO |
| Ligation 10X | Tris HCl 500 mM pH 7.5, 100 mM MgCl$_2$, 100 mM DTT, 10 mM ATP, 250 µg/ml BSA |

II—Preparation and Test of the Plasmids

1) Construction

The gene of the intein 2 of the Tfu DNA polymerase (itfu2) (Accession number in Gene library: Z69822) was inserted between the restriction sites Nde I and Sal 1 of the vector pET26b+ in order to create the plasmid pET26-Tfu2 represented in FIG. 3. In similar fashion, the alcohol dehydrogenase gene (adh) of *Thermococcus hydrothermalis* was inserted between the restriction sites Nde I and Bam HI of the vector pET26B+ in order to create the vector pADH, and the genes of the P-lactamase TEM-1 (bla) of *Escherichia coli* (9), and of the Green Fluorescent Protein (gfp) of *Aequorea Victoria* (6) and of the lipase B of *Candida Antarctica* (lipB) (Accession number Y14015 in Gene library) were inserted respectively between the restriction sites Nde I and Eco RI of the vector pET26b+, in order to create the plasmids pADH, pTEM, pGFP and pLIP represented in FIG. 3. For each one of these four genes, the restriction site Nde I is over located with the codon ATG of the translation initiation.

Each construction was verified by several restriction profile analyses. 200 µl of XL1-Blue chimiocompetent cells (1) were transformed with 10 ng of each plasmid by a thermal shock (2), and the cells thus transformed were spread out on a solid LB medium containing 60 µg/ml of kanamycin and 12.5 µg/ml of tetracycline. Starting from a clone of each one of these transformations, a plasmidic DNA maxipreparation was carried out with a TIP100 type column (QIAGEN). After precipitation in isopropanol, each plasmidic DNA sample was resuspended in 100 µl of buffer T. The concentration of these plasmidic DNAs was evaluated by a spectrophotometric measurement at 260 nm. The purity of each plasmidic DNA was verified by depositing 0.2 µl of each of the vectors on agarose gel TBE 1%.

2) In Vivo Expression Tests-activity Tests

-pTEM: 200 µl of BL21 DE3 (pLysS) chimiocompetent cells were transformed with 10 ng of the pTEM plasmid by a thermal shock, and the cells thus transformed were spread out on a solid LB medium containing 60 µg/ml of kanamycin, 20 µg/ml of chloramphenicol, 32 µg/ml of IPTG and 100 µg/ml of ampicillin. After incubation one night at 37° C., very numerous colonies could be observed on the Petri dish, thereby revealing that the TEM-1 gene of the plasmid pTEM is expressed and functional, and that it confers ampicillin resistance.

-pGFP: 200 µl of BL21 DE3 (pLysS) chimiocompetent cells were transformed with 10 ng of the plasmid pGFP by a thermal shock, and the cells thereby transformed were spread out on a solid LB medium containing 60 µ g/ml of kanamycin, 20 µg/ml of chloramphenicol and 32 µg/ml of IPTG. After incubation one night at 37° C., very numerous colonies could be observed on the Petri dish. All of these reacted to ultraviolet excitation (at about 400 nm) by emitting a green fluorescent light, which permitted verification that the gfp gene of the plasmid pGFP is expressed and functional.

Figure 4:
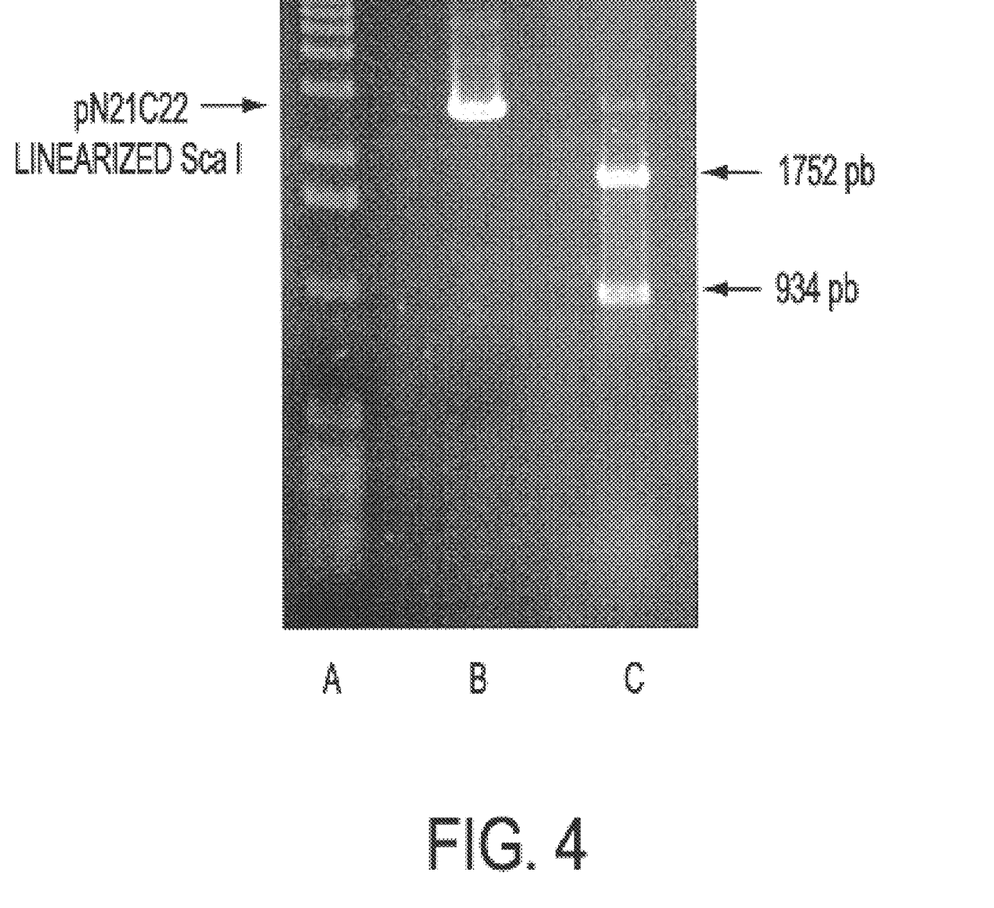
FIG. 4 represents the activity of the intein 2 of a DNA polymerase of *Thermococcus fumicolans* (Tfu) obtained in vivo by expression cloning. Track A: molecular weigh marker 1 Kb. Track B: reaction without enzyme. Track C: reaction with intein 2.

-pET26-Tfu2: 200 µl of BI21 DE3 (pLysS) chimiocompetent cells were transformed with 10 ng of the plasmid pET26-Tfu2 by a thermal shock, and the cells transformed thereby were spread out on a solid LB medium containing 60 µg/ml of kanamycin and 20 µg/ml of chloramphenicol. A culture carried out starting from a clone of this transformation was induced at $DO_{600\ nm}$=0.5 with 0.5 mM of IPTG for two hours at 37° C. After centrifugation, the bacterial precipitate was resuspended in 20 mM sodium phosphate buffer pH 7.5, and a cellular lysate was obtained after to several cycles of freezing/thawing. The intein 2 was then purified on a Qfast-Flow column with a NaCl gradient. The activity of this enzyme was tested according to the following protocol: 1 µl of the elution fraction having the highest pure enzyme concentration was diluted one hundred times. One µl of this dilution was incubated 15 minutes at 70° C. with 3 µl of IT2 buffer and 220 ng of the pHS2-22-21 plasmid, linearized with the restriction enzyme Sca I, in a final volume of 30 µl. 15 µl of this digestion mixture were deposited on an agarose gel TBE 1%. After migration and staining with ethidium bromide, the gel was exposed to ultraviolet. As shown in FIG. 4, the analysis of this gel reveals the presences of two bands of respectively 934 bp and 1752 bp, corresponding to the cutting of the pHS2-22-21 vector (Sca I linearized) by the intein 2. The gene itfu2 of the plasmid pET26-Tfu2 is therefore expressed and its product, the intein 2, is active.

-pADH: 200 µl of BL21 DE3 (pLysS) chimiocompetent cells were transformed with 10 ng of the pADH plasmid by a thermal shock, and the cells thus transformed were spread out on a solid LB medium containing 60 µg/ml of kanamycin and 20 µg/ml of chloramphenicol. A culture carried out starting from a clone of this transformation was induced at $DO_{600\ nm}$=0.6 with 1 mM of IPTG for three hours at 37° C. After centrifugation, the bacterial precipitate was taken up in a sodium phosphate buffer 50 mM-$MgCl_2$ 10 mM pH 8.0, and the cellular lysate was obtained by incubating 30 minutes over ice in the presence of 1 mg/ml of lysozyme, 10 µg/ml of RNAse A and 100 µg/ml of DNAse I. The centrifugation supernatant of this extraction step was incubated 30 minutes at 50° C., and centrifuged again. The supernatant of this last step was used as an enzymatic extract for the measurements of activity. A negative control was made up in parallel by carrying out a similar extraction on a culture of BL21 DE3 (pLysS) cells excluding plasmid. The alcohol dehydrogenase activity was tested by following with a spectrophotometer the reduction kinetics of the NADP to NADPH at 340 nm. For this, 10 µl of the enzymatic extract, or of the control, were incubated at 50° C. for five minutes with 500 µl of TADH buffer and 490 µl of water. Under these conditions, an activity of 15.6 UDO/miniml of enzymatic extract was detected, against 0 UDO/min/ml for the control. The pADH plasmid gene adh is therefore expressed and its product, the alcohol dehydrogenase, is active.

III—Protein Expression Trials In Vitro (EPIV) with a Translation Extract Prepared from Mesophilic Strains (37° C.)

4 µg of each vector were precipitated in the presence of one tenth volume of sodium acetate 3 M pH 6.0, and two volumes of absolute alcohol. The precipitates were rinsed with 70% ethanol in order to eliminate any trace of salts. Each precipitated DNA was resuspended in 4 µl of buffer T.

This DNA is incubated two hours at 37° C. in a protein expression mixture in vitro containing 0.1 mM of each one of the 20 amino acids, 20 µl of "S30 Premix" extract and 15 µl of "T7 S30 extract" (PROMEGA) in a final volume of 50 µl. The "S30 Premix" and "T7 S30 extract" extracts contain all the elements necessary for an in vitro transcription reaction coupled with a translation reaction, notably: T7 RNA polymerase, CTP, UTP, GTP, ATP, tRNAs, EDTA, folic acid and appropriate salts. The translation extract was produced according to the procedure described by Zubay (10) from an *Escherichia coli* B strain deficient in endoproteinase OmpT and in Ion protease, which better stabilizes the proteins expressed in vitro.

A negative control was prepared by incubating ultra pure sterile water in place of the DNA in the transcription-translation mixture. The positive control was formed by incubating 2 µg of PinPoint™ plasmid.

The EPIV reactions were preserved on ice until the enzymatic activity of each sample could be evaluated.

IV—Measurement of the Activitives

1) Mesophilic Enzymes a) GFP Activity

Figure 5:
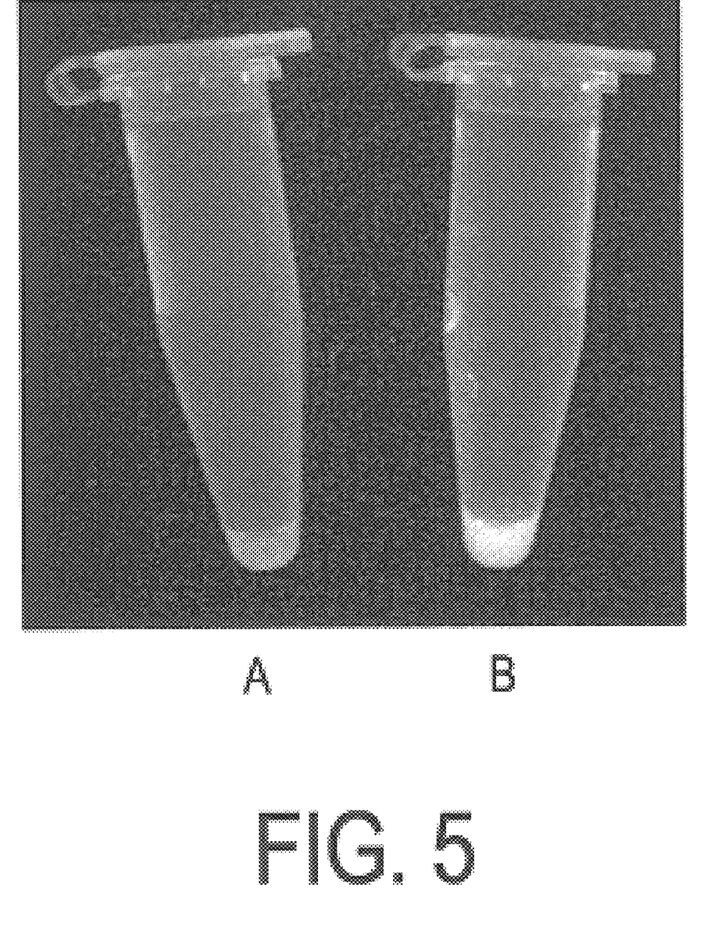
FIG. 5 represents the activity of the GFP produced by EPIV reaction (Emission of fluorescence followed by an exposure at about 400 nm) with mesophilic translation extracts. Tube A: EPIV reaction with water (control). Tube B: EPIV reaction with the vector pGFP.

FIG. 5 shows the tube containing the product of the EPIV reaction with the pGFP vector that was exposed to ultraviolet at about 400 nm, beside the tube containing the control reaction. Only the tube containing the EPIV reaction of the pGFP plasmid emitted a green fluorescent light. The EPIV reaction therefore permits the production of a GFP protein having a fluorescent activity.

b) β-lactamase Activity

The β-lactamase activity was evaluated by following by spectrophotometry the degradation kinetics of nitrocephine, a chromogenic cephalosporin, at 486 nm (5). For this, 5, 10, or 20 μl of the EPIV reaction with the pTEM vector are incubated 2 minutes at 37° C. in a BETA buffer, final volume 1 ml. The average activity of the EPIV reaction with the pTEM vector could be estimated at 8.9 UDO/min/ml of extract, against 0.6 UDO/min/ml of extract with the control EPIV reaction. The protein expression reaction in vitro therefore permitted the synthesis of an active β-lactamase, capable of degrading the nitrocephine in vitro.

The control PinPoint™ vector carries the bla gene under the control of its promoter. However, the β-lactamase activity of the EPIV reaction with this vector was tested and evaluated at 6 UDO/min/ml of extract. It is useful to note that the addition of rifampicine at 1 ng/μl, the RNA polymerase inhibitor of E. coli, does not significantly modify the in vitro expression of the β-lactamase with the PinPoint™ vector. The bla gene of the PinPoint™ vector, located 2123 bp downstream of the T7 promoter is therefore transcribed and translated effectively. This implies that a gene located 2000 bp downstream of a T7 promoter is effectively transcribed and translated during an EPIV reaction.

2) Thermophilic Enzymes a) Intein 2 Activity

The EPIV reaction with the pET26-Tfu2 vector was tested in order to know if an active intein 2 could be produced. For this, 5 μl of this EPIV reaction were incubated 20 minutes at 70° C. with 220 ng of pHS2-22-21 vector, linearized with Sca 1, and 3 μl of IT2 buffer in a final volume of 30 μl. A negative control was formed by replacing the 5 μl of the EPIV reaction with water. The positive control contained 1 μl of the purified intein 2 fraction produced in vitro diluted to $1/100^{th}$. Finally, a specificity control was made by incubating 5 μl of the EPIV reaction not having received any DNA.

Figure 6:
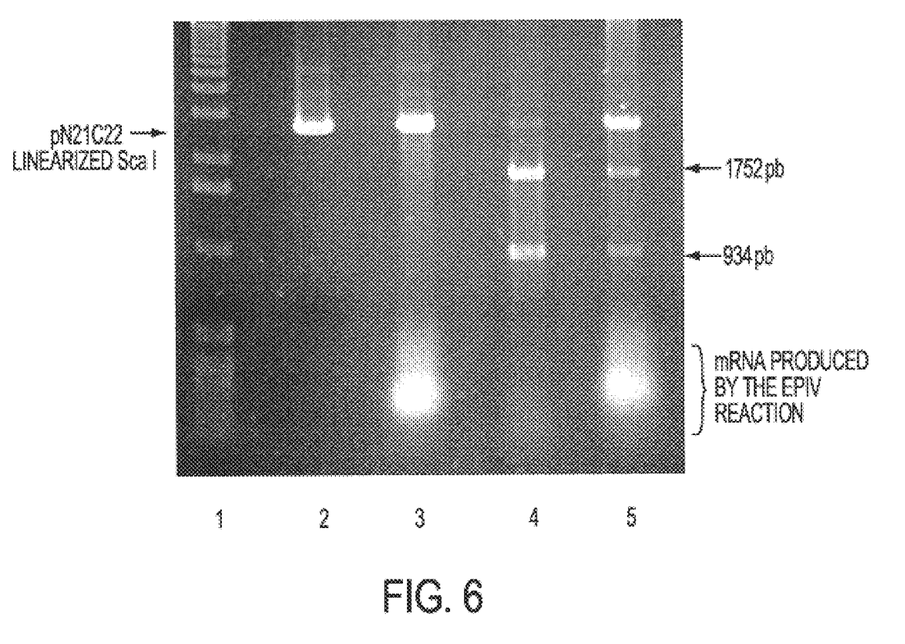
FIG. 6 represents the activity of the intein 2 of the Tfu DNA polymerase produced by EPIV reaction with mesophilic-type translation extracts. Track 1: molecular weigh marker 1 Kb. Track 2: T− (reaction without enzyme). Track 3: Blank (reaction with EPIV extract without DNA). Track 4: T+ (reaction with intein 2 produced in vivo). Track 5: Test (reaction with intein 2 produced by EPIV (pET26-Tfu2)).

After incubation, the four trials underwent a phenol-chloroform extraction and an ethanol precipitation, followed by rinsing with 70% ethanol in order to eliminate salts. Each precipitate was taken up in 10 μl of buffer T, and 8 μl were deposited on an agarose TBE 1% gel. After migration and staining with ethidium bromide, the gel was exposed to ultraviolet in order to analyze the restriction profiles. The appearance of bands at 934 and 1752 bp on track 5 of FIG. 6, identical to the bands of track 4 (positive control) reveals that the intein 2 is indeed produced by the EPIV reaction, and that this enzyme is active. In addition, the EPIV reaction is specific since no other digestion band can be observed on the control of track 3.

b) Alcohol Dehydrogenase Activity

Using spectrophotometry, the alcohol dehydrogenase activity was tested by following the reduction kinetics from NADP to NADPH at 340 nm. For this, 5, 10, or 15 μl of the EPIV reaction with the vector pADH, or without DNA, were incubated at 50° C. for five minutes with 500 μl of TADH buffer in a final volume of 1 ml. Under these conditions, the average activity of the EPIV reaction with the pADH vector was estimated at 2.3 UDO/min/ml of extract, against 0.32 UDO/min/ml of extract for the control (EPIV reaction with water). The ADH of Thermococcus hydrothermalis (accession number Y14015 in Gene library) was therefore produced in an active form during the EPIV reaction.

3) Psychrophyle Enzyme

The lipase activity was tested by following, the spectrophotometric degradation kinetics of a chromogenic lipid (1,2-O-dilauryl-rac-glycero-3-glutaric acid-resorufin ester) at 572 nm. For this, 5 μl of the EPIV reaction with the PLIP vector, or without DNA were incubated at 70° C. for fifteen minutes in the reaction buffer in the presence of 100 μg of substrate. Under these conditions, the activity of the EPIV reaction with the pLIP vector was estimated at 0.50 UDO/min/ml of extract against 0.04 UDO/min/ml of extract for the control. The lipase B of Candida Antarctica (Eukaryotic organism) was therefore produced in active form during the EPIV reaction.

Figure 7:
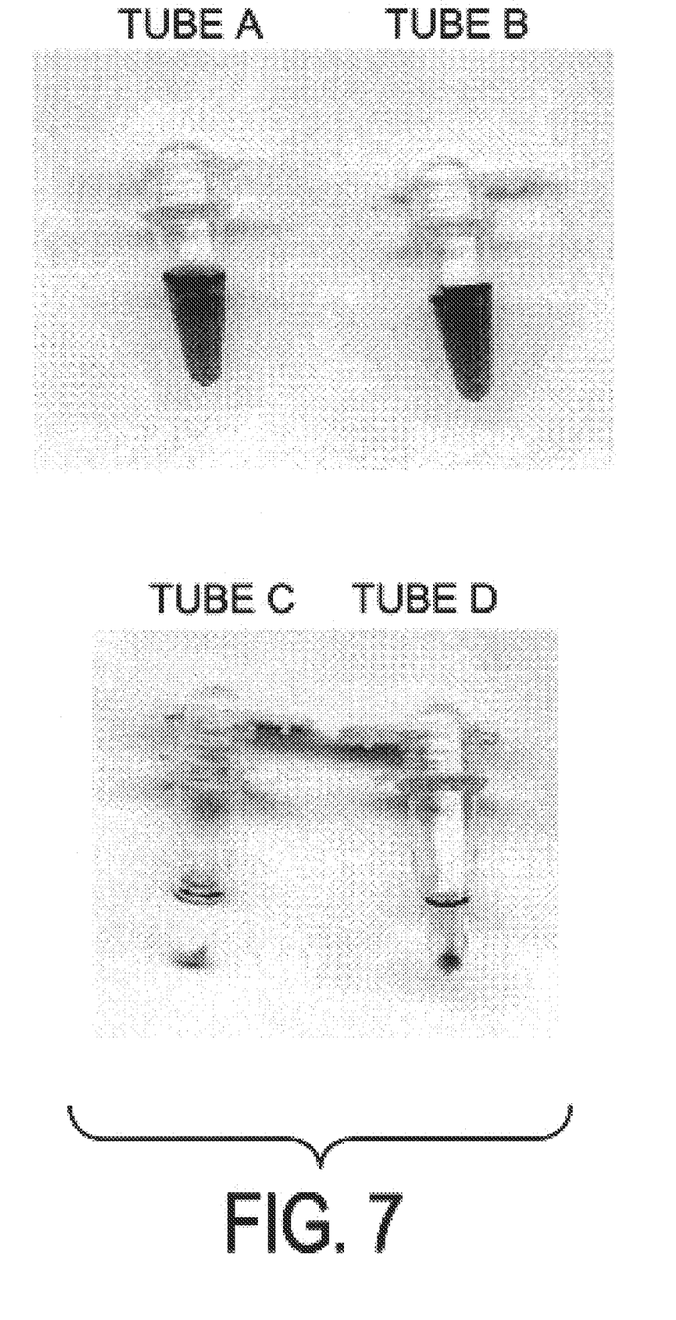
FIG. 7 represents the detection of the activity of a thermophilic enzyme by using a mesophilic translation extract containing said activity. Tube A: EPIV reaction with water (control) incubated at 37° C., Tube B: EPIV reaction incubated at 37° C., Tube C: EPIV reaction with water (control) incubated at 70° C. after centrifugation. Tube D: EPIV reaction incubated at 70° C. after centrifugation.

V—Using a Translation Extract Containing a Mesophilic Activity for Detecting a Thermophilic Property The beta-galactosidase gene of Thermotoga neapolitana was inserted in a vector containing the T7 RNA polymerase transcription promoter. The vector thus obtained was used for carrying out an EPIV reaction with a translation extract of an E. coli strain possessing a beta-galactosidase activity. In parallel, an EPIV reaction without DNA was carried out. By incubating a fraction of each one of the EPIV reactions at 37° C. in the presence of Xgal at 37° C. in a sodium phosphate buffer (50 mM, pH 7), the two tubes changed to a blue color in minutes (cf FIG. 7 tubes A and B). By incubating a fraction of each one of the EPIV reactions in the presence of Xgal under the same conditions but at 70° C., only the tube corresponding to the EPIV reaction with the plasmid coding for the thermophilic beta-galactosidase changed to the blue color pellet (cf FIG. 7 tubes C and D: these two tubes were centrifuged in order to color the proteins of the mesophilic translation extract which precipitated as a consequence of their thermic denaturation during the activity test at 70° C.). The mesophilic beta-galactosidase activity is no longer detectable at this temperature (thermal denaturation of the mesophilic beta-galactosidase). It is therefore possible to use a translation extract containing a property similar to the sought-after property if this property is not detectable under the detection conditions of the sought-after property.

VI—Translation Extract Prepared from Extremophilic Organisms

Translation extracts of other organisms and in particular of extremophilic organisms can be prepared starting from cells according to one of the procedures described by Zubay (1973) (10) or by Pratt (1984) (7). The speeds of centrifugation, the conditions of cell breakage and the different reaction or preparation buffers will be adjusted for each type of translation extract by systematic trials. By thus practicing the range of translation extracts, it becomes possible to translate a gene whatever be its genetic origin: the process of the invention therefore permits having a correspondence between the translation system and the punctuation of expression of the gene coding for the sought-after property.

BIBLIOGRAPHIC REFERENCES

1) Hanahan D., (1985), Techniques for transformation of Excherichia coli, in DNA cloning: a practical approach. Glover D. M. (Ed.), IRL Press, Oxford vol. I, 109–135.

2) Maniatis T., Fristch E. F. and Sambrook J., (1982). Molecular cloning. A laboratory Manual, Cold Spring Harbor Laboratory, Cold Spring Harbor, N.Y.
3) Masson J. M., Meuric P., Grunstein M., Abelson J. and Miller H. J., (1987), Expression of a set of synthetic suppressor tRNA$^{Phe}$ genes in *Saccharomyces cerevisiae*, Proc. Natl. Acad. Sci. UAS, 84, 6815–6819.
4) Normanly J., Masson J. M., Kleina L, G., Abelson J. and Miller J. H., 1986, Construction of two *Escherichia coli* amber suppressor genes: tRNA$^{Phe}$CUA and tRNA$^{Cys}$CUA, Proc, Natl. Acad. Sci. USA, 83, 6548–6552.
5) O'Callaghan C. H., Morris A., Kirby S. M. and Shingler A. H., 1972, Novel methel for detection of beta-lactamase by using a chromogenic cephalosporin substrate, Antimicrob. Agents Chemother., 1. 283–288.
6) Prasher D. C.. Eckenrode V. K., Ward W. W., Prendergast F. G. and Cormier M. J., 1992 Primary structure of the *Aequorea Victoria* green-fluorescent protein, Gene, 111, 229–233.
7) Pratt J. M., 1984, Coupled transcription-translation in prokaryotic cell-free systems, Transcription and Translation: A practical approach, Hames B. D. and Higgins S. J. Eds, JRL Press.
8) Studier F. W. and Moffatt B. A., 1986, Use of bacteriophage T7 RNA polymerase to direct selective high-level expression of cloned genes, J. Mol. Biol, 189, 113–130.
9) Sutcliffe J. G., 1978, Nucleotide sequence of the ampicillin resistance gene of *Escherichia coli* plasmid pBR322, Proc. Natl. Acad. Sci. USA, 75. 3737–3741.
10) Zubay G., 1973, In vitro synthesis of protein in microdial systems. Ann. Rev. Geneti., 7, 267–287.

What is claimed is:

1. A method for identifying a selected function associated with one or more unknown nucleic acids in a biological sample, comprising the steps of:
   (i) expressing in vitro said one or more unknown nucleic acids;
   (ii) characterizing the function of said one or more unknown expressed nucleic acids; and
   (iii) determining whether said characterized function corresponds to said selected function;
   wherein the sample comes from or comprises an unknown organism.

2. A method for identifying a selected function associated with one or more unknown nucleic acids in a biological sample, comprising the steps of:
   (i) expressing in vitro said one or more unknown nucleic acids,
   (ii) characterizing the function of said one or more unknown expressed nucleic acids, and
   (iii) determining whether said characterized function corresponds to said selected function; and
   wherein expressing said nucleic acids in vitro comprises:
   a) preparing fragments of said unknown nucleic acids from said sample,
   b) combining said fragments with a plasmidic vector,
   c) isolating said combined fragments,
   d) transcribing said combined fragments in vitro to obtain transcripts, and
   e) translating said transcripts,
   wherein the plasmidic vector permits no expression of said nucleic acids in vitro.

3. The method of claim 1 or 2, further comprising determining the sequence of a nucleic acid having a function corresponding to said selected function.

4. The method of claim 1 or 2, wherein said unknown nucleic acids are not identified, referenced or characterized in a DNA database.

5. The method of claim 1 or 2, wherein said unknown nucleic acids comprise a plurality of different unknown nucleic acids that are expressed at step (i).

6. The method of claim 5 or 2, wherein characterizing the function comprises characterizing in vitro the function of said plurality of unknown nucleic acids.

7. The method of claim 1 or 2, wherein characterizing the function comprises simultaneously testing in vitro the expressed nucleic acids for different properties indicative of a single specific biological activity.

8. The method of claim 1 or 2, wherein characterizing the function comprises simultaneously testing in vitro the expressed nucleic acids for at least one property indicative of a plurality of specific biological activities.

9. The method of claim 1 or 2, wherein characterizing the function comprises testing in vitro the expressed nucleic acids for a ribozyme function, a tRNA function, an enzymatic function or an affinity function.

10. The method of claim 2, wherein the sample comes from or comprises an unknown organism.

11. The method of claim 1 or 2, wherein the sample comes from or comprises a plurality of unknown organisms.

12. The method of claim 1 or 2, wherein the sample comprises or comes directly from a prokaryotic organism, eukaryotic cell, plant cell, virus, soil, blood, water sample, biopsy, or a combination of any of the foregoing.

13. The method of claim 1 or 2, wherein the sample is a crude sample comprising different prokaryotic organisms, different eukaryotic cells, different plant cells, different viruses, soil, blood, a biopsy, or a combination of any of the foregoing constituents, wherein a plurality of said constituents are unknown.

14. The method of claim 1 or 2, wherein the sample comes from or comprises an extremophilic organism.

15. The method of claim 1 or 2, wherein the nucleic acids in the sample consist essentially of genomic DNA.

16. The method of claim 1 or 2, wherein the sample comprises different microorganisms or extracts therefrom, and wherein said microorganisms or extracts are not isolated from each other in the method.

17. The method of claim 16, wherein the method is carried out entirely on a solid support.

18. The method of claim 17, wherein said solid support comprises a chip, a membrane, or a nanotitration plate.

19. The method of claim 18, wherein the method screens substantially 100 percent of the sample's biodiversity for said function in about 5 to 10 days.

20. The method of claim 18, wherein said method is automated.

21. The method of claim 1, wherein expressing said nucleic acids in vitro comprises:
   a) preparing fragments of said unknown nucleic acids from said sample;
   b) combining said fragments with a vector molecule;
   c) isolating said combined fragments; and
   d) transcribing said combined fragments in vitro to obtain transcripts; and
   e) translating said transcripts.

22. The method of claim 21 or 2, wherein the transcribing of said combined fragments occurs at the same time as the translating of said transcripts.

23. The method of claim 21, wherein the vector molecule is a plasmidic vector.

24. The method of claim 23, wherein the plasmidic vector permits no expression of said nucleic acids in vitro.

25. The method of claim 21 or 2, wherein the fragments of step b) are inserted in said plasmidic vector at a cloning site, and wherein said plasmidic vector comprises at least one transcription promoter.

26. The method of claim 25, wherein the transcription promoter is T3, T7, SP6, Qβ, λ phage, or a combination thereof.

27. The method of claim 25, wherein the transcription promoter comprises an RNA polymerase promoter flanking one or both sides of the cloning site, and the plasmidic vector optionally further comprises an RNA polymerase terminator flanking one or both sides of the cloning site or flanking the RNA polymerase promoter.

28. The method of claim 27, wherein the promoter or terminator are non-functional in a microorganism used for isolating said combined fragments.

29. The method of claim 21 or 2, wherein said sample comes from or comprises an unknown prokaryotic organism and the fragments prepared at step a) are 1 to 10 kb in length.

30. The method of claim 21 or 2, wherein said sample comes from or comprises an unknown eukaryotic organism and said fragments prepared at step a) are 40 to several hundreds of kilobases in length.

31. The method of claim 21 or 2, wherein the in vitro transcribing is completed by a splicing and maturation reaction of the transcript.

32. The method of claim 21 or 2, wherein said isolating of step c) is carried out by transforming a host cell with the vector of step b) to create a clone library, and then extracting the vector from the clone library.

33. The method of claim 21 or 2, wherein said combining of step b) is performed essentially by ligation.

34. The method of claim 21 or 2, wherein said translating comprises using a translation extract that originates from said sample or shares an origin with said sample.

35. The method of claim 21 or 2, wherein said translating comprises using a universal translation extract that is independent of the sample.

36. The method of claim 21 or 2, wherein said translating comprises using a mixture of translation extracts.

37. The method of claim 21 or 2, wherein said translating comprises using a translation extract comprising a tRNA specific for a codon, a substance favoring a refolding of a protein translated from the transcripts, a substance favoring the effective maturation of said protein, or a combination of any of the foregoing.

* * * * *

UNITED STATES PATENT AND TRADEMARK OFFICE
CERTIFICATE OF CORRECTION

PATENT NO.    : 6,514,703 B1                                        Page 1 of 1
DATED         : February 4, 2003
INVENTOR(S)   : Dupret et al.

It is certified that error appears in the above-identified patent and that said Letters Patent is hereby corrected as shown below:

Column 17,
Line 64, delete "*in vitro*" and replace with -- *in vivo* --.

Column 19,
Line 2, delete "*in vitro*" and replace with -- *in vivo* --.

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,514,703 B1
DATED         : February 4, 2003
INVENTOR(S)   : Dupret et al.

Page 1 of 1

It is certified that error appears in the above-identified patent and that said Letters Patent is hereby corrected as shown below:

<u>Title page,</u>
Item [30], Foreign Application Priority Data, delete "Feb. 12, 1998" and replace with -- Aug. 12, 1998 --.

Signed and Sealed this

Twenty-seventh Day of January, 2004

JON W. DUDAS
*Acting Director of the United States Patent and Trademark Office*